US012616778B2

(12) United States Patent
Yang et al.

(10) Patent No.: US 12,616,778 B2
(45) Date of Patent: May 5, 2026

(54) COMPOSITE ULTRATHIN COATING FILM WITH INHIBITORY ACTIVITY AGAINST HYPERINFLAMMATORY RESPONSE AND BACTERIA, IMPLANT INCLUDING SAME, AND PREPARATION METHOD THEREFOR

(71) Applicant: THE INDUSTRY & ACADEMIC COOPERATION IN CHUNGNAM NATIONAL UNIVERSITY (IAC), Daejeon (KR)

(72) Inventors: Sung Yun Yang, Daejeon (KR); Su Jin Lee, Daejeon (KR); Dong Woon Kim, Sejong (KR); Sang-Ha Oh, Daejeon (KR)

(73) Assignee: THE INDUSTRY & ACADEMIC COOPERATION IN CHUNGNAM NATIONAL UNIVERSITY (IAC), Daejeon (KR)

( * ) Notice: Subject to any disclaimer, the term of this patent is extended or adjusted under 35 U.S.C. 154(b) by 515 days.

(21) Appl. No.: 18/569,988

(22) PCT Filed: Feb. 14, 2022

(86) PCT No.: PCT/KR2022/002125

§ 371 (c)(1),
(2) Date: Dec. 13, 2023

(87) PCT Pub. No.: WO2022/182035

PCT Pub. Date: Sep. 1, 2022

(65) Prior Publication Data

US 2024/0216578 A1 Jul. 4, 2024

(30) Foreign Application Priority Data

Feb. 26, 2021 (KR) ........................ 10-2021-0026441

(51) Int. Cl.

| | |
|---|---|
| ***A61L 27/34*** | (2006.01) |
| ***A61F 2/00*** | (2006.01) |
| ***A61L 27/18*** | (2006.01) |
| ***A61L 27/20*** | (2006.01) |
| ***A61L 27/54*** | (2006.01) |

(52) U.S. Cl.

CPC ............ *A61L 27/34* (2013.01); *A61F 2/0077* (2013.01); *A61L 27/18* (2013.01); *A61L 27/20* (2013.01); *A61L 27/54* (2013.01); *A61F 2210/0076* (2013.01); *A61L 2300/236* (2013.01); *A61L 2300/404* (2013.01); *A61L 2400/02* (2013.01); *A61L 2400/18* (2013.01); *A61L 2420/08* (2013.01)

(58) Field of Classification Search

None

See application file for complete search history.

(56) References Cited

FOREIGN PATENT DOCUMENTS

| | | | |
|---|---|---|---|
| KR | 10-2010-0122880 | A | 11/2010 |
| KR | 1081336 | B1 | 11/2011 |
| KR | 10-1783308 | B1 | 9/2017 |

OTHER PUBLICATIONS

Burke, S. E. et al., "Swelling behavior of hyaluronic acid/polyallylamine hydrochloride multilayer films", Biomacromolecules, 2005, vol. 6, No. 3, pp. 1419-1428.

Tarannum, N. et al. "Synthesis, characterization and applications of copolymer of β-cyclodextrin: A review", Journal of Polymer Research, 2020, vol. 27, No. 4, pp. 1-30.

Thomsen, H. et al., "Delivery of cyclodextrin polymers to bacterial biofilms—An exploratory study using rhodmnine labelled cyclodextrins and multiphoton microscopy", International Journal of Pharmaceutics. 20 17, vol. 531, No. 2, pp. 650-657.

*Primary Examiner* — Patrick T Lewis

(74) *Attorney, Agent, or Firm* — Bridgeway IP Law Group, PLLC; Jihun Kim

(57) ABSTRACT

A composite ultra-thin coating film with hypersensitivity inflammatory reaction inhibition and antibacterial activity, an implant comprising the same, and a method for preparing the same are described. The composite ultra-thin coating film can be applied to medical silicone-based polymers and exhibits excellent antibacterial activity and inhibits deformed cell proliferation so that hypertrophic tissue is not formed and there is no cytotoxicity.

15 Claims, 5 Drawing Sheets

Compared to uncoated (P<0.0001) one way ANOVA

COMPOSITE ULTRATHIN COATING FILM WITH INHIBITORY ACTIVITY AGAINST HYPERINFLAMMATORY RESPONSE AND BACTERIA, IMPLANT INCLUDING SAME, AND PREPARATION METHOD THEREFOR

TECHNICAL FIELD

The present invention relates to a composite ultra-thin coating film with hypersensitivity inflammatory reaction inhibition and antibacterial activity, an implant comprising the same, and a method for preparing the same.

BACKGROUND ART

Due to the rapid aging of Korea in recent years, the population aged 65 or older is expected to account for 20.3% in 2025, and the use of implants is expected to increase for replacement of organs that have lost function due to aging and accidents, as well as for health promotion and beauty. In modern medicine, many defects in the human or animal body can be compensated for or minimized by their effectiveness by the use of implants. For example, it is well known that space holders for vertebrae or intervertebral discs serve to put the vertebral bodies or intervertebral discs in place. In a further example, a fixation or stabilization system may be mentioned for the spinal columns in which pedicle screws are fixed to the vertebrae and connected to each other via connecting rods, and therefore, the spacing and arrangement of the vertebrae may be arranged or fixed with respect to each other. For all implants, it is important that materials that are compatible with human or animal organs, that is, materials that do not cause rejection reaction due to decomposition phenomenon or do not produce harmful substances in the organ are used. Therefore, the choice of materials for implants is practically limited.

A silicone material is the most representative soft material in addition to hard metallic materials among the materials used in implants. Silicone has been known to be the most common and stable material to date, but after insertion into the human body after surgery/procedures, it still causes deformation of the tissue at the insertion site due to frequent inflammatory reactions so that there is controversy over safety issues due to reoperation and removal surgery.

Meanwhile, Korean Patent No. 1081336 has disclosed the synthesis of metal or sol-gel nanoparticles using a polymer electrolyte membrane with nanopores as a template and its application to biosensors, and Korean Patent Publication No. 2012-0124769 has disclosed a silicone implant material coated with a biodegradable polymer and a preparation method thereof, but a composite ultra-thin coating film with hypersensitivity inflammatory reaction inhibition and antibacterial activity according to the present invention, an implant comprising the same, and a method for preparing the same have not yet been disclosed.

DISCLOSURE

Technical Problem

An object of the present invention is to provide, as a composite ultra-thin coating film that can be applied to medical silicone-based polymers, a composite ultra-thin coating film with hypersensitivity inflammatory reaction inhibition and antibacterial activity, which exhibits excellent antibacterial activity, and inhibits deformed cell proliferation so that hypertrophic tissue is not formed, and there is no cytotoxicity.

Another object of the present invention is to provide a composite ultra-thin coating film with hypersensitivity inflammatory reaction inhibition and antibacterial activity, which can inhibit biofilm formation caused by the proliferation of *S. epidermidis*, which is best known as a risk factor for film construction after silicone-based polymer insertion, and can reduce film construction due to increased thickness of the film, an implant including the same, and a method for preparing the same.

Technical Solution

In order to achieve the above object, the present invention is a composite ultra-thin coating film including: an inner layer in which materials selected from the group consisting of a hyaluronic acid polymer (HA), a polymer represented by the following Formula 1, and poly(allylamine hydrochloride) (PAH) are alternately laminated; and an outermost layer in contact with cells, wherein the outermost layer may be laminated with a hyaluronic acid polymer (HA) or a polymer represented by the following Formula 1:

[Formula 1]

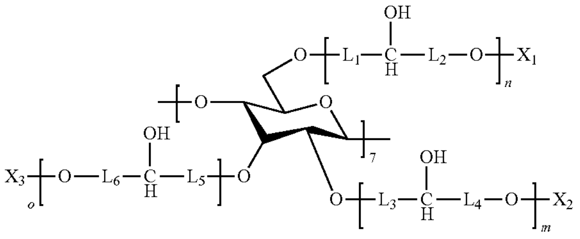

[Formula 2]

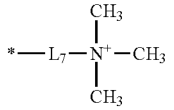

[Formula 3]

$$*—L_8—COO^-H^+$$

where,

* refers to a part that is combined, n, m, and o are the same as or different from each other and are each independently an integer of 1 to 100, $L_1$ to $L_8$ are the same as or different from each other, and are each independently a single bond or a substituted or unsubstituted alkylene group having 1 to 10 carbon atoms, and $X_1$ to $X_3$ are the same as or different from each other, and are each independently selected from the group consisting of cyclodextrin, a compound represented by Formula 2 above, and a compound represented by Formula 3 above.

The compound represented by Formula 1 above is a cationic polymer (Cat-CyD) including the compound represented by Formula 2 above, and may be alternately laminated with hyaluronic acid (HA) or poly(allylamine hydrochloride) (PAH).

The compound represented by Formula 1 above is an anionic polymer (Ani-CyD) including the compound represented by Formula 3 above, and may be alternately laminated with the cationic polymer (Cat-CyD).

The inner layer may be [PAH/HA], [PAH/Cat-CyD], [Cat-CyD/HA], or [Cat-CyD/Ani-CyD] laminated in a plurality.

The inner layer may be formed by laminating [PAH/HA], [PAH/Cat-CyD], [Cat-CyD/HA] or [Cat-CyD/Ani-CyD] in a plurality, and then additionally laminating [Cat-CyD].

The inner layer may have a pH of 3 to 5.

The composite ultra-thin coating film may inhibit the formation of a biofilm produced by *Staphylococcus epidermidis.*

The composite ultra-thin coating film may inhibit malformed cell proliferation.

The composite ultra-thin coating film may have a thickness of 20 nm or less.

A method for preparing a composite ultra-thin coating film according to another embodiment of the present invention may include steps of: forming an inner layer by alternately laminating materials selected from the group consisting of a hyaluronic acid polymer (HA), a polymer represented by the following Formula 1, and poly(allylamine hydrochloride) (PAH); and forming an outermost layer in contact with cells by laminating the hyaluronic acid polymer (HA) or the polymer represented by the following Formula 1:

[Formula 1]

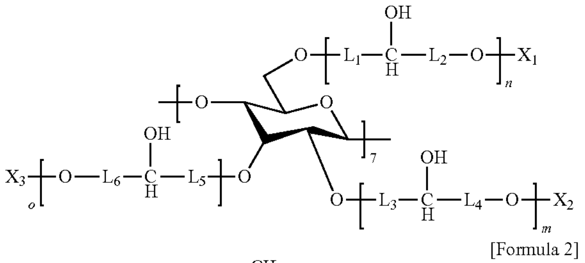

[Formula 2]

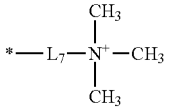

[Formula 3]

$*—L_8—COO^-H^+$ where,

* refers to a part that is combined, n, m, and o are the same as or different from each other and are each independently an integer of 1 to 100, $L_1$ to $L_8$ are the same as or different from each other, and are each independently a single bond or a substituted or unsubstituted alkylene group having 1 to 10 carbon atoms, and $X_1$ to $X_3$ are the same as or different from each other, and are each independently selected from the group consisting of cyclodextrin, a compound represented by Formula 2 above, and a compound represented by Formula 3 above.

The inner layer may be formed under conditions of pH 3 to 5.

An implant according to another embodiment of the present invention may include a substrate and the composite ultra-thin coating film according to claim 1 formed on a surface of the substrate.

The substrate may be a silicone-based polymer or metal.

A method for manufacturing an implant on which a composite ultra-thin coating film is formed according to another embodiment of the present invention may include steps of: forming an inner layer by alternately laminating materials selected from the group consisting of a hyaluronic acid polymer (HA), a polymer represented by the following Formula 1, and poly(allylamine hydrochloride) (PAH) on a substrate; and forming an outermost layer in contact with cells by laminating the hyaluronic acid polymer (HA) or the polymer represented by the following Formula 1:

[Formula 1]

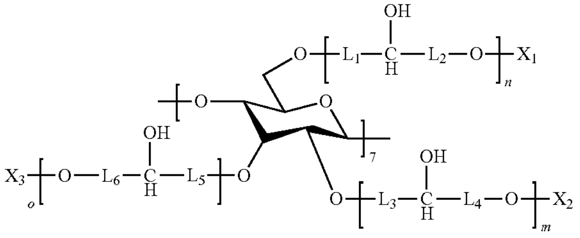

[Formula 2]

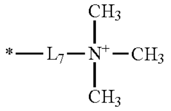

[Formula 3]

$*—L_8—COO^-H^+$ where,

* refers to a part that is combined, n, m, and o are the same as or different from each other and are each independently an integer of 1 to 100, $L_1$ to $L_8$ are the same as or different from each other, and are each independently a single bond or a substituted or unsubstituted alkylene group having 1 to 10 carbon atoms, and $X_1$ to $X_3$ are the same as or different from each other, and are each independently selected from the group consisting of cyclodextrin, a compound represented by Formula 2 above, and a compound represented by Formula 3 above.

A contact lens for ophthalmic surgery according to another embodiment of the present invention may include a silicone-based polymer substrate and the composite ultra-thin coating film according to claim 1 formed on a surface of the substrate.

In the present invention, "alkyl" refers to a monovalent substituent derived from a straight-chain or branched-chain saturated hydrocarbon having 1 to 40 carbon atoms. Examples thereof may include methyl, ethyl, propyl, isobutyl, sec-butyl, pentyl, iso-amyl, hexyl, etc., but are not limited thereto.

In the present invention, "substitution" means changing a hydrogen atom bonded to a carbon atom of a compound to another substituent, and the position to be substituted is not limited as long as it is the position where the hydrogen atom is substituted, that is, a position where the substituent can be substituted, and if two or more substituents are substituted, two or more substituents may be the same as or different from each other. The substituents may be substituted with one or more substituents selected from the group consisting of hydrogen, a cyano group, a nitro group, a halogen group, a hydroxy group, a carboxy group, an alkoxy group having 1 to 10 carbon atoms, an alkyl group having 1 to 30 carbon atoms, an alkenyl group having 2 to 30 carbon atoms, an alkynyl group having 2 to 24 carbon atoms, a heteroalkyl group having 2 to 30 carbon atoms, an aralkyl group having 6 to 30 carbon atoms, an aryl group having 5 to 30 carbon atoms, a heteroaryl group having 2 to 30 carbon atoms, a heteroarylalkyl group having 3 to 30 carbon atoms, an alkoxy group having 1 to 30 carbon atoms, an alkylamino group having 1 to 30 carbon atoms, an arylamino group having 6 to 30 carbon atoms, an aralkylamino group having 6 to 30 carbon atoms, and a heteroarylamino group having 2 to 24 carbon atoms, and when they are substituted with a plurality of substituents, they may be the same as or different from each other, and are not limited to the above examples.

Advantageous Effects

The present invention is a composite ultra-thin coating film that can be applied to medical silicone-based polymers, and it can exhibit hypersensitivity inflammatory reaction inhibition and antibacterial activity, which exhibit excellent antibacterial activity, and inhibit deformed cell proliferation so that hypertrophic tissue is not formed, and there is no cytotoxicity.

In addition, it can inhibit biofilm formation caused by the proliferation of *S. epidermidis*, which is best known as a risk factor for film construction after silicone-based polymer insertion, and reduce film construction due to increased thickness of the film.

BEST MODE

Figure 1:
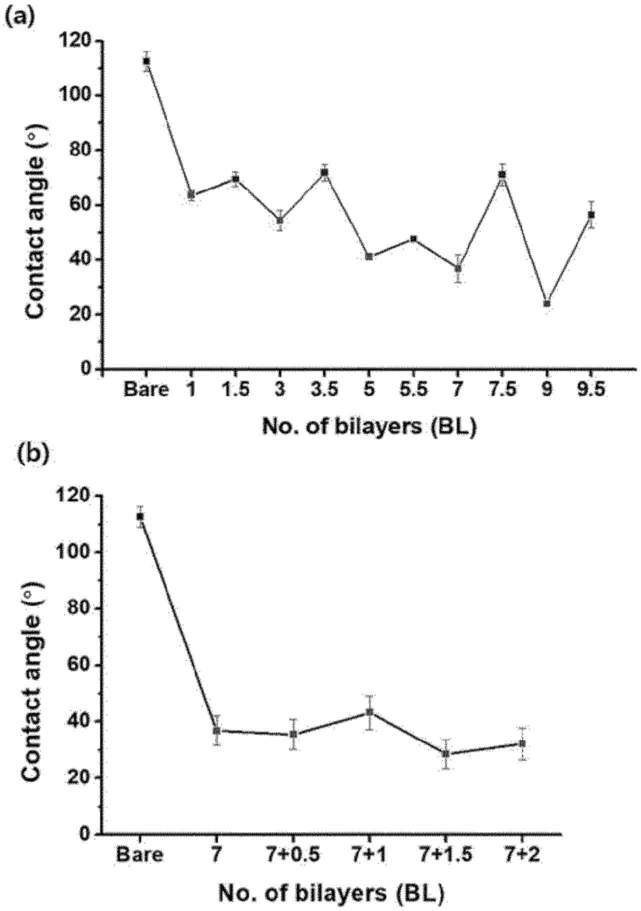
FIG. 1 relates to changes in water contact angles when a composite ultra-thin coating film is applied to a silicone-based polymer according to one embodiment of the present invention.

The present invention is a composite ultra-thin coating film including: an inner layer in which materials selected from the group consisting of a hyaluronic acid polymer (HA), a polymer represented by the following Formula 1, and poly(allylamine hydrochloride) (PAH) are alternately laminated; and an outermost layer in contact with cells, wherein the outermost layer may be laminated with a hyaluronic acid polymer (HA) or a polymer represented by the following Formula 1:

[Formula 1]

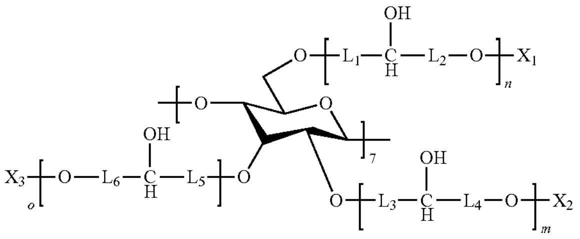

[Formula 2]

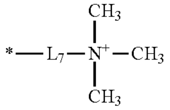

[Formula 3]

$$*—L_8—COO^-H^+$$

where,

* refers to a part that is combined, n, m, and o are the same as or different from each other and are each independently an integer of 1 to 100, $L_1$ to $L_8$ are the same as or different from each other, and are each independently a single bond or a substituted or unsubstituted alkylene group having 1 to 10 carbon atoms, and $X_1$ to $X_3$ are the same as or different from each other, and are each independently selected from the group consisting of cyclodextrin, a compound represented by Formula 2 above, and a compound represented by Formula 3 above.

MODE FOR INVENTION

Hereinafter, embodiments of the present invention will be described in detail so that those skilled in the art to which the present invention pertains can easily implement it. However, the present invention may be implemented in many different forms and is not limited to the embodiments described herein.

The present invention relates to a composite ultra-thin coating film including: an inner layer in which materials selected from the group consisting of a hyaluronic acid polymer (HA), a polymer represented by the following Formula 1, and poly(allylamine hydrochloride) (PAH) are alternately laminated; and an outermost layer in contact with cells, wherein the outermost layer is laminated with a hyaluronic acid polymer (HA) or a polymer represented by the following Formula 1:

[Formula 1]

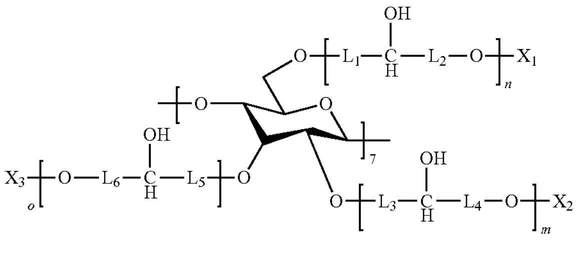

-continued

[Formula 2]

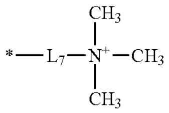

[Formula 3]

$*—L_8—COO^-H^+$ where,

* refers to a part that is combined, n, m, and o are the same as or different from each other and are each independently an integer of 1 to 100, $L_1$ to $L_8$ are the same as or different from each other, and are each independently a single bond or a substituted or unsubstituted alkylene group having 1 to 10 carbon atoms, and $X_1$ to $X_3$ are the same as or different from each other, and are each independently selected from the group consisting of cyclodextrin, a compound represented by Formula 2 above, and a compound represented by Formula 3 above.

The $L_1$ to $L_6$ may be the same as or different from each other, and may each independently be an alkylene group having 1 to 10 carbon atoms, and preferably a methylene group.

The polymer represented by Formula 1 above is a polymer containing cyclodextrin, and may contain a quaternary ammonium salt represented by Formula 2 above (Cat-CyD), or contain an anionic substituent represented by Formula 3 above (Ani-CyD).

$L_7$ may be an alkylene group having 1 to 10 carbon atoms, and preferably an ethylene group.

$L_8$ may be an alkylene group having 1 to 10 carbon atoms, and preferably a methylene group.

Cyclodextrin may be α-cyclodextrin, β-cyclodextrin, or γ-cyclodextrin. The repeating unit of Formula 1 above refers to one repeating unit of cyclodextrin and relates to cyclodextrin containing 7 repeating units.

As described above, $X_1$ to $X_3$ may be combined with a compound represented by Formula 2 or Formula 3 above, but may also be combined with cyclodextrin.

The hyaluronic acid polymer (HA) is a compound represented by the following Formula 4:

[Formula 4]

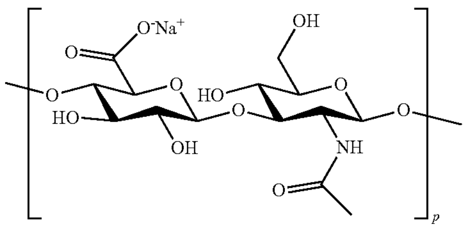

where, p is an integer of 1 to 100.

Poly(allylamine hydrochloride) (PAH) is a compound represented by the following Formula 5:

[Formula 5]

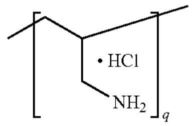

where, q is an integer of 1 to 100.

PAH forming the inner layer is a cationic polymer compound, HA is an anionic polymer compound, and the compound represented by Formula 1 above may be a cationic polymer compound (Cat-CyD) or an anionic polymer compound (Ani-CyD).

The compound represented by Formula 1 above may be a cationic polymer compound (Cat-CyD) when the quaternary ammonium salt represented by Formula 2 is combined, and it may be an anionic polymer compound (Ani-CyD) when the compound represented by Formula 3 above is combined.

The inner layer may include a bilayer as one repeating unit, and the bilayer may include the cationic polymer compound and the anionic polymer compound described above as one set.

As will be described later, the substrate on which the coating film is formed may exhibit anionic properties. The surface of the substrate may exhibit anionic properties, or —OH groups may be formed through plasma treatment, etc. A layer may be formed by primarily treating the substrate surface as described above with a cationic polymer compound, and then another layer may be formed by treating the substrate surface with an anionic polymer compound, thereby forming one bilayer.

The inner layer may be a plurality of [PAH/HA], [PAH/Cat-CyD], [Cat-CyD/HA], or [Cat-CyD/Ani-CyD] stacked. [PAH/HA] means that poly(allylamine hydrochloride) and a hyaluronic acid polymer are repeatedly stacked as one layer, [PAH/Cat-CyD] means that poly(allylamine hydrochloride) and a polymer represented by Formula 1 containing the cationic substituent are repeatedly stacked as one layer, [Cat-CyD/HA] means that a polymer represented by Formula 1 containing the cationic substituent and a hyaluronic acid polymer are repeatedly stacked as one layer, and [Cat-CyD/Ani-CyD] means that a polymer represented by Formula 1 containing the cationic substituent and a polymer represented by Formula 1 containing the anionic substituent are repeatedly stacked as one layer.

For example, a layer in which a pair of different ionic polymers such as Cat-CyD and HA are combined and stacked is called one bilayer, indicating the number of stacks. In other words, if Cat-β-CyD and HA are stacked in one bilayer, it is indicated as [Cat-β-CyD/HA]1.

The multilayer film combination is also indicated by indicating the pH of the polymer solution used for stacking the multilayer film. For example, if the pH of both PAH/HA polyelectrolytes is adjusted to 4.5 and a total of 7 bilayers are stacked, it may be expressed as $[PAH(4.5)/HA(4.5)]_7$.

It is possible to form a composite multilayer thin film coating layer using not only two of polymer electrolytes but also three or more of polymer electrolytes. At first, it is stacked with PAH/HA, and then when stacked with Cat-CyD and HA, it may be expressed as [PAH/HA]m+[Cat-β-CyD/HA]n.

More specifically, it is stacked in a structure of [PAH/HA]r, [PAH/Cat-CyD]r, or [Cat-CyD/HA]r; or after it is stacked in a structure of [PAH/HA]r, [PAH/Cat-CyD]r, or [Cat-CyD/HA]r, [Cat-CyD] may be additionally stacked. r represents the number of stackings of [PAH/HA], [PAH/Cat-CyD], or [Cat-CyD/HA], and is 1 to 100.

m is an integer; or it may be displayed as a number of 'an integer+0.5'. When displayed as an integer+0.5, it indicates the case that stacking has been made as many times as the number of repeating units, one additional layer is stacked once more and completed. For example, [Cat-CyD/HA]7.5 means that [Cat-CyD/HA] is stacked 7 times, and Cat-CyD is stacked once more on the outermost layer.

The inner layer may have a pH of 3 to 5. Specifically, after the inner layer is stacked to $[PAH(4.5)/HA(4.5)]_7$ or $[Cat\text{-}CyD(3.0)/HA(4.5)]_7$, [Cat-CyD] is additionally stacked once, but it is not limited thereto. The numbers 4.5 and 3.0 in the parentheses above refer to pH.

The composite ultra-thin coating film can suppress the formation of a biofilm produced by *Staphylococcus epidermidis*, the composite ultra-thin coating film can inhibit malformed cell proliferation, and the composite ultra-thin coating film may have a thickness of preferably 20 nm or less, more preferably 16 to 20 nm, but is not limited thereto.

The composite ultra-thin coating film is preferably a composite ultra-thin coating film that can be coated on a substrate that can be used for implants, or contact lenses for use in the eye. The substrate is preferably a silicone-based polymer or metal, but is not limited thereto. The metal is preferably any one selected from titanium (Ti), silicon (Si), iron (Fe), and stainless steel, but is not limited thereto.

Furthermore, a method for preparing a composite ultra-thin coating film according to another embodiment of the present invention may include steps of: forming an inner layer by alternately laminating materials selected from the group consisting of a hyaluronic acid polymer (HA), a polymer represented by the following Formula 1, and poly (allylamine hydrochloride) (PAH); and forming an outermost layer in contact with cells by laminating the hyaluronic acid polymer (HA) or the polymer represented by the following Formula 1:

[Formula 1]

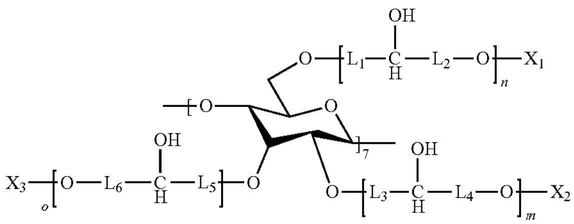

[Formula 2]

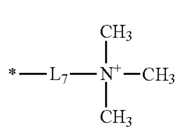

[Formula 3]

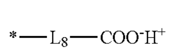

* refers to a part that is combined, n, m, and o are the same as or different from each other and are each independently an integer of 1 to 100, $L_1$ to $L_8$ are the same as or different from each other, and are each independently a single bond or a substituted or unsubstituted alkylene group having 1 to 10 carbon atoms, and $X_1$ to $X_3$ are the same as or different from each other, and are each independently selected from the group consisting of cyclodextrin, a compound represented by Formula 2 above, and a compound represented by Formula 3 above.

The inner layer may be formed under conditions of pH 3 to 5. Specifically, after the inner layer is stacked to $[PAH(4.5)/HA(4.5)]_7$ or $[Cat\text{-}CyD(3.0)/HA(4.5)]_7$, [Cat-CyD] is additionally stacked, but it is not limited thereto. The numbers 4.5 and 3.0 in the parentheses above refer to pH.

Further, an implant according to another embodiment of the present invention may include: a substrate; and the composite ultra-thin coating film formed on a surface of the substrate.

The substrate is preferably a silicone-based polymer or metal, and the metal is preferably any one implant material selected from titanium (Ti), silicon (Si), iron (Fe), and stainless steel, but is not limited thereto.

Furthermore, a method for manufacturing an implant on which a composite ultra-thin coating film is formed according to another embodiment of the present invention may include steps of: forming an inner layer by alternately laminating materials selected from the group consisting of a hyaluronic acid polymer (HA), a polymer represented by the following Formula 1, and poly(allylamine hydrochloride) (PAH) on a substrate; and forming an outermost layer in contact with cells by laminating the hyaluronic acid polymer (HA) or the polymer represented by the following Formula 1:

[Formula 1]

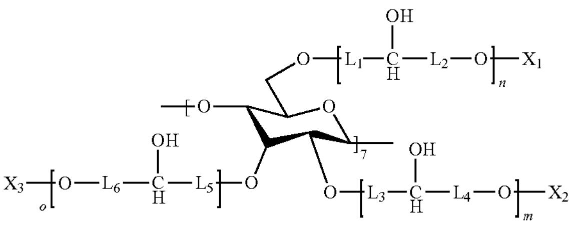

[Formula 2]

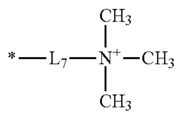

[Formula 3]

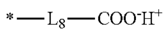

where,

* refers to a part that is combined, n, m, and o are the same as or different from each other and are each independently an integer of 1 to 100, $L_1$ to $L_8$ are the same as or different from each other, and are each independently a single bond or a substituted or unsubstituted alkylene group having 1 to 10 carbon atoms, and $X_1$ to $X_3$ are the same as or different from each other, and are each independently selected from the group consisting of cyclodextrin, a compound represented by Formula 2 above, and a compound represented by Formula 3 above.

Furthermore, a contact lens for ophthalmic surgery according to another embodiment of the present invention may include a silicone-based polymer substrate and the composite ultra-thin coating film formed on a surface of the substrate.

Hereinafter, the present invention will be described in more detail using Examples. These Examples are only for illustrating the present invention in more detail, and it is obvious to those skilled in the art that the scope of the present invention is not limited thereto.

Preparation Example 1

Preparation of Cationic Cat-CyD Polymer

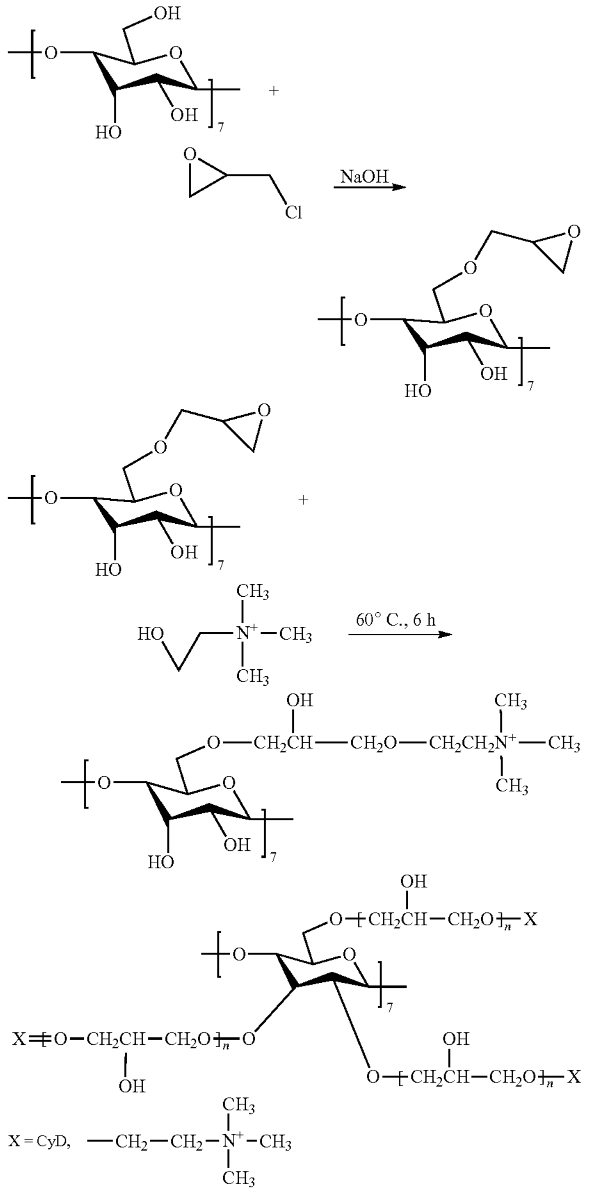

After 1 g (0.025 mol) of NaOH was dissolved in 20 ml of deionized (DI) water in a 50 ml round flask to prepare a 0.022 mol % (0.048 wt %) of a NaOH aqueous solution, 1.135 g (0.001 mol) of β-CyD was put thereinto, and the mixture was stirred and dissolved at 25° C. for 18 hours. When stirring was completed, the round flask containing the reactants was moved to an oil bath and the hot plate temperature was set to 60° C. When the set temperature was reached, 1.388 g (1.2 ml, 0.015 mol) of Epichlorohydrin (EP) was added thereto at a rate of about 0.1 ml/min, 0.2792 g (0.002 mol) of Choline chloride (CC) was quickly put into the reactor right away, and it was closed with a joint stopper. While polymerization was in progress, the inside of the reactor was maintained at 60° C., and the reaction was allowed to proceed for 24 hours in this state, and then the pH of the reactant was adjusted to neutral using a 12N HCl aqueous solution to complete the polymerization. To purify the obtained solution, dialysis was performed for 48 hours using MWCO 1000 and 3500 membranes depending on the use. The solution obtained in this way was prepared in a pure powder form through a freeze-drying process.

Yield: 0.74 g (22.2%)

Preparation Example 2

Preparation of Anionic β-CyD Polymer (Ani-CyD)

After 1 g (0.025 mol) of NaOH was dissolved in 20 ml of DI water, 1.135 g (0.001 mol) of β-CyD was dissolved in the NaOH solution. The mixed solution was stirred at 25° C. for 24 hours. 0.189 g (0.002 mol) of chloroacetic acid (CA) was rapidly injected into the solution, and 1.388 g (1.2 ml, 0.015 mol) of EP was added thereto at a flow rate of 0.1 ml/min. After EP feeding was completed, the mixture was heated at 60° C. for 6 hours. After 6 hours, the heated mixture was neutralized with a 3N HCl solution to stop polymerization. The obtained solution was dialyzed for 24 hours using a dialysis membrane with a molecular weight cutoff of 3000 to 3500. Yield: 0.6 g (~20%).

Preparation Example 3

Formation of Composite Ultra-Thin Coating Film

A hyaluronic acid polymer (HA) and poly(allylamine hydrochloride) (PAH) were purchased and used. A Cat-CyD polymer was synthesized in the same manner as in Preparation Example 1 above.

Each polymer electrolyte was adjusted to a concentration of 0.01M using secondary distilled water, and the pH was maintained at 3.0 or 4.5. The washed and dried silicone substrate was treated with plasma for about 30 seconds to instantly increase its hydrophilicity, and then immersed in a polymer electrolyte solution to lay up the polymer on the surface.

Specifically, the silicone sample with —OH group oxidized by plasma was first immersed in a cationic PAH solution for 15 minutes to induce PAH adsorption, and then washed twice using secondary distilled water to remove residual PAH. PAH is well adsorbed to silicone and can help form a multilayer film coating to be introduced later. In the same way as introducing PAH, anionic HA is introduced alternately with PAH to form a [PAH/HA] coating film, or cationic Cat-β-CyD and HA are alternately laminated, and the immersion and recovery are repeated so that they are laminated to the desired thickness.

Example 1

Confirmation of Contact Angle Changes and Surface Morphologies

The results of confirming water contact angles according to the lamination of the composite ultra-thin coating film of the present invention on a silicone-based polymer are as shown in FIG. 1.

It was confirmed that the contact angle of the silicone-based polymer before coating was 100 to 120°, which was strongly hydrophobic, and it was confirmed that, when a coating layer of [PAH (4.5)/HA (4.5)]$_m$ (m is 1 to 9.5) was formed, the contact angle was significantly reduced (FIG.

1A), and when coated with a $[PAH(4.5)/HA(4.5)]_7$+[Cat-CyD(3.0)/HA(4.5)]$_m$ (m is 0.5 to 2) film, the contact angle decreased to 20 to 400 (FIG. 1B). These results mean that when the coating film of the present invention is formed, hydrophilicity is greatly increased.

A PAH (4.5)/HA (4.5) coating film was first introduced on the surface of the silicone-based polymer, and then Cat-CyD (3.0) was additionally formed. The Cat-CyD polymer may exhibit antibacterial properties and interaction with cells due to substituted amine groups while increasing hydrophilicity. From the first lamination, the contact angle was already about 40°, showing excellent hydrophilicity, and it was confirmed that there was no further significant change even when the lamination was repeated three or more times. Accordingly, the Cat-CyD polymer layer was coated once as the outermost layer.

Figure 2:
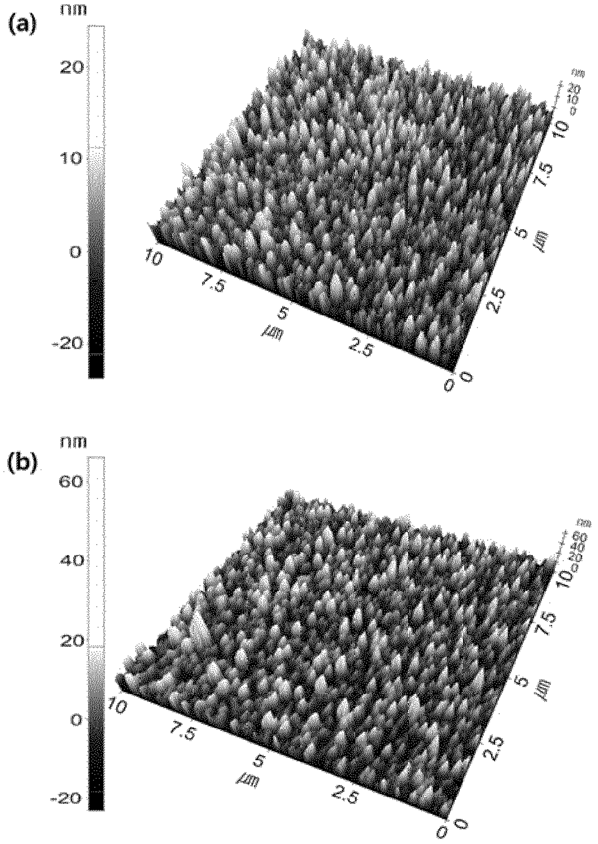
FIG. 2 shows results of confirming the surface morphology of a composite ultra-thin coating film measured by AFM according to one embodiment of the present invention.

In addition, as shown in FIG. 2, as a result of analyzing the morphology of the sample surface using atomic force microscopy (AFM), very small and fine protruding structures were shown when both of the HA layer and the Cat-CyD polymer were the outermost layer in the $[PAH(4.5)/HA(4.5)]_7$+Cat-CyD coating layer.

HA is a polymer of 1.3 to 2.0 MDa, PAH has a molecular weight of 150,000, and Cat-CyD has a molecular weight of 8,000.

Example 2

Confirmation of Cell Proliferation and Cytotoxicity

In HEK293 cells, a kidney-derived cell line, the degree of cell adsorption and cell proliferation rate of $[PAH(4.5)/HA(4.5)]_7$ and $[PAH(4.5)/HA(4.5)]_7$+Cat-CyD coating film according to the present invention were confirmed.

Figure 3:
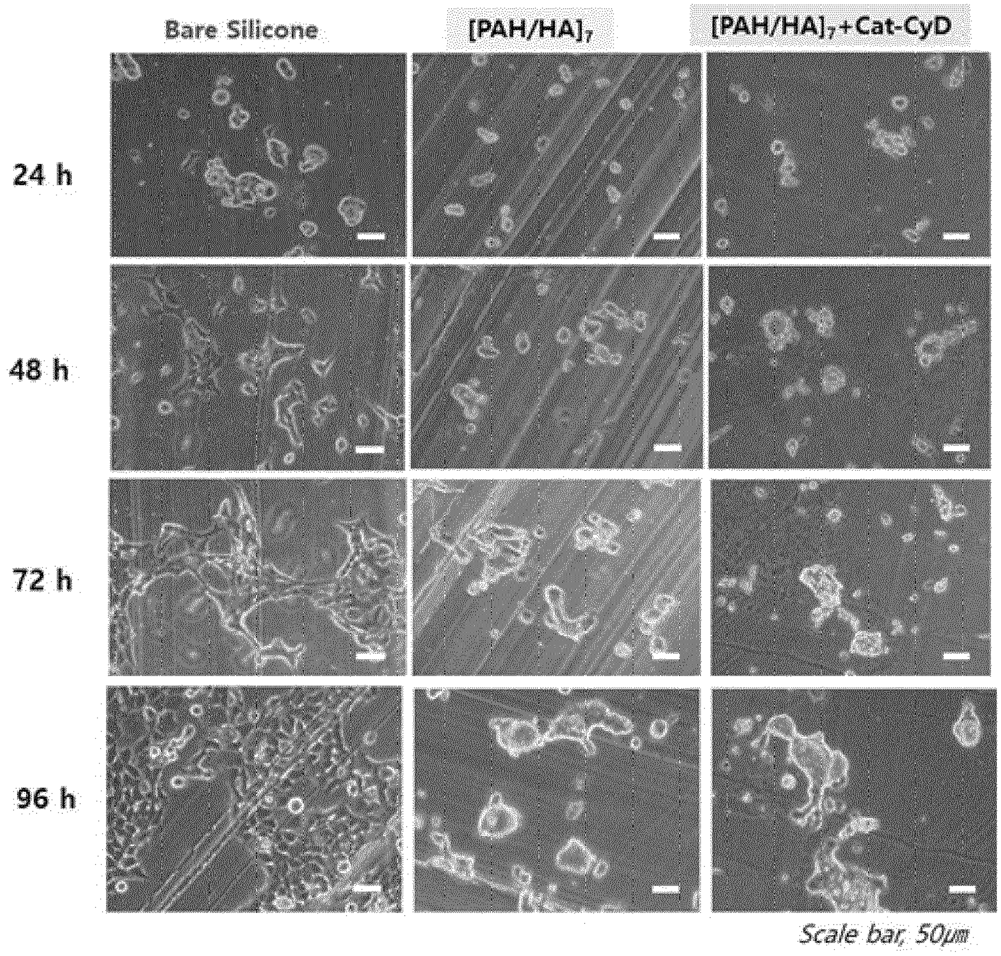
FIG. 3 shows results of confirming HEK293 cell adsorption and proliferation when a composite ultra-thin coating film according to one embodiment of the present invention is applied to the surface of a silicone-based polymer.
Figure 4:
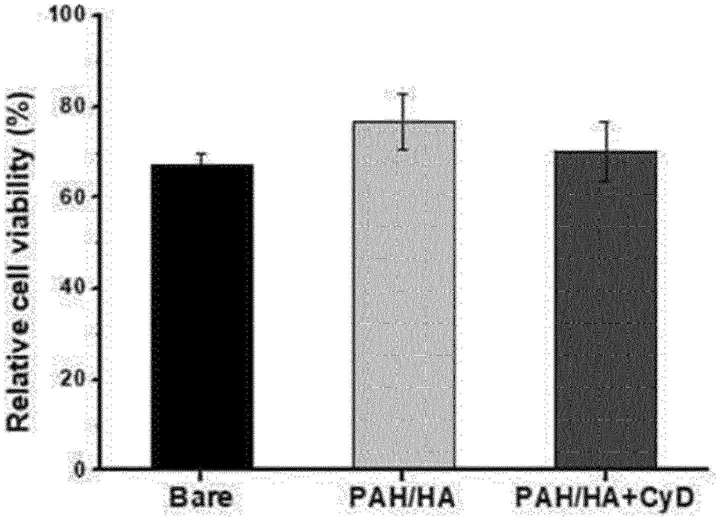
FIG. 4 shows MTT results confirming the cell survival rate of HEK293 cells when a composite ultra-thin coating film according to one embodiment of the present invention is applied to the surface of a silicone-based polymer.

As disclosed in FIG. 3, it was confirmed that not only the degree of cell adsorption decreased, but also the cell proliferation rate decreased for 24 to 96 hours in the silicone-based polymer-treated group having the $[PAH(4.5)/HA(4.5)]_7$ and $[PAH(4.5)/HA(4.5)]_7$+Cat-CyD coating films of the present invention formed thereon compared to the group treated with the silicone-based polymer. To confirm whether such a decrease in cell proliferation was due to cytotoxicity, 3-(4,5-Dimethylthiazol-2-yl)-2,5-Diphenyltetrazolium Bromide (MTT) assay was performed. As a result, as disclosed in FIG. 4, it was shown that there were almost no changes in cell viability, and it was determined that there was no cytotoxicity.

Example 3

Confirmation of Changes in Surrounding Tissues

A silicone-based polymer having the composite ultra-thin coating film of the present invention formed thereon was inserted into a mouse, and 30 days later, an incision was made to confirm changes in the surrounding tissues into which the silicone-based polymer was inserted using Hematoxylin and eosin (H&E) staining.

Figure 5:
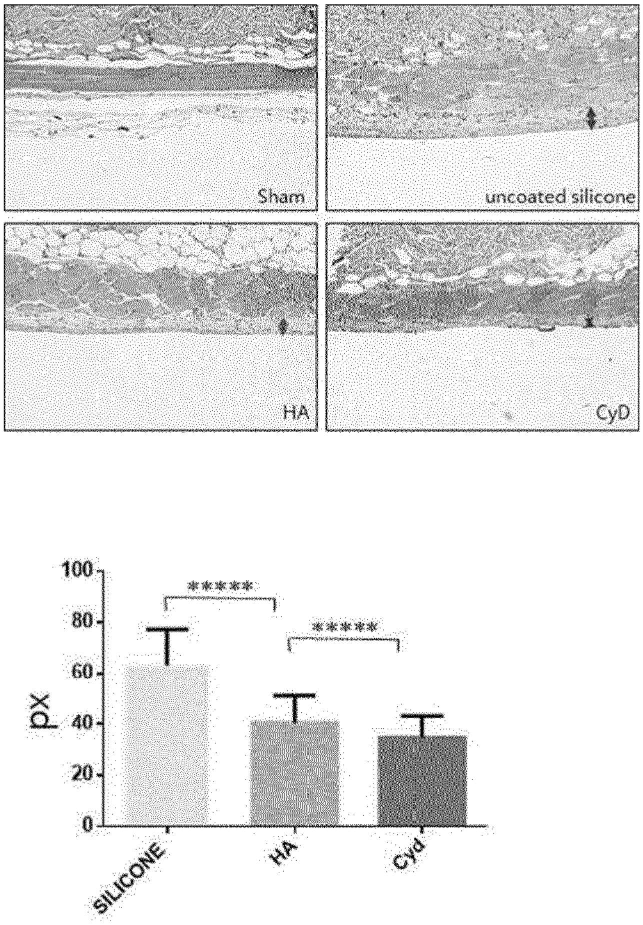
FIG. 5 shows results of confirming tissue changes after inserting a silicone-based polymer in which a composite ultra-thin coating film according to one embodiment of the present invention is applied to the surface of a silicone-based polymer into an experimental mouse.

As a result, it could be confirmed that the surrounding tissues were enlarged in the group having an uncoated silicone-based polymer inserted thereinto compared to the normal group (Sham), and when the silicone-based polymer having $[PAH(4.5)/HA(4.5)]_7$ and $[PAH(4.5)/HA(4.5)]_7$+Cat-CyD coating films of the present invention was inserted, the surrounding tissue condition of a level similar to that of the normal group could be observed, and it could be confirmed that it was in a state of being closer to the normal group when the silicone-based polymer having the $[PAH(4.5)/HA(4.5)]_7$+Cat-CyD coating film was inserted than when the silicone-based polymer having the $[PAH(4.5)/HA(4.5)]_7$ coating film was inserted (FIG. 5).

Example 4

Confirmation of Antibacterial Activity

In order to confirm the antibacterial activity of the silicone-based polymer having the composite ultra-thin coating film of the present invention formed thereon, *Staphylococcus epidermidis* was cultured and the absorbance at 570 nm was measured to confirm the degree of proliferation of *Staphylococcus epidermidis*.

Figure 6:
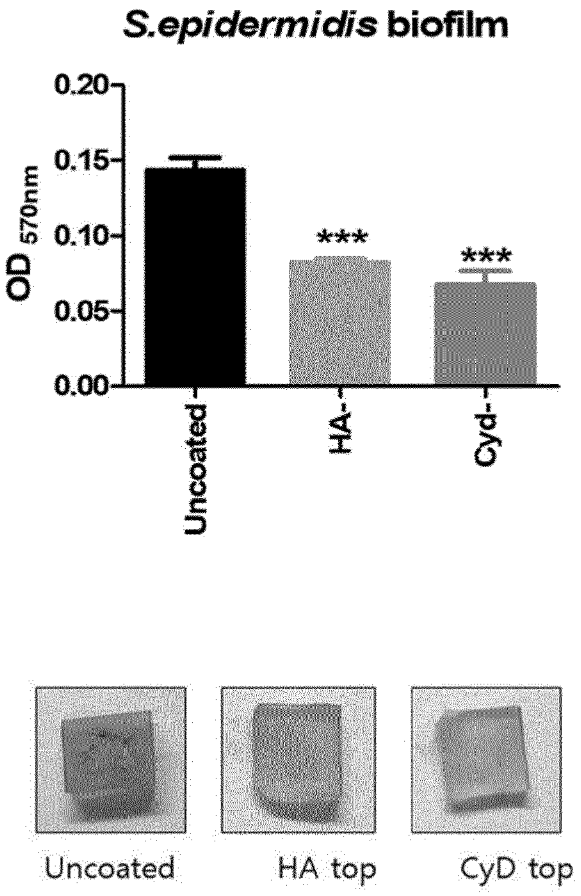
FIG. 6 confirms the effect of inhibiting the biofilm formation of *S. epidermidis* of a silicone-based polymer in which a composite ultra-thin coating film according to one embodiment of the present invention is applied to the surface of a silicone-based polymer.

As a result, as disclosed in FIG. 6, it was confirmed that the degree of proliferation of *Staphylococcus epidermidis* was small in the silicone-based polymer having the $[PAH(4.5)/HA(4.5)]_7$ and $[PAH(4.5)/HA(4.5)]_7$+Cat-CyD coating films according to the present invention compared to an uncoated one.

Although preferred embodiments of the present invention have been described in detail above, the scope of rights of the present invention is not limited thereto, and various modifications and improved forms made by those skilled in the art using the basic concept of the present invention defined in the following claims also fall within the scope of the rights of the present invention.

Related research of the present invention was conducted with the support of the following tasks:

[Assignment serial number] 1711112898
[Assignment number] 2020R1A2C2009666
[Name of Ministry] Ministry of Science and ICT
[Name of assignment management (professional) organization] National Research Foundation of Korea
[Research Project Name] Mid-career researcher support project
[Research Assignment Name] Development of a cell-based verification platform using multifunctional polymer hybrid material research
[Contribution rate] 8/10
[Name of assignment carrying out organization] Chungnam National University
[Research period] 2020 Mar. 1~2021 Feb. 28.
[Assignment serial number] 1711110145
[Assignment number] 2019R1A2C2004884
[Name of Ministry] Ministry of Science and ICT
[Name of assignment management (professional) organization] National Research Foundation of Korea
[Research Project Name] Mid-career researcher support project
[Research Assignment Name] Development of microglial-specific neuropathic pain control technology using CRISPR/Cas9 system and nano fusion technology
[Contribution rate] 1/10
[Name of assignment carrying out organization] Chungnam National University
[Research period] 2020 Mar. 1~2021 Feb. 28.
[Assignment serial number] 1465032250
[Assignment number] HI20C2088020020
[Name of Ministry] Ministry of Health and Welfare
[Name of assignment management (professional) organization] Korea Health Industry Development Institute
[Research Project Name] Health and medical technology research and development project
[Research Assignment Name] Digital healthcare field based on convergence optical technology
[Contribution rate] 1/10

[Name of assignment carrying out organization] Chungnam National University Hospital

[Research period] 2020 Nov. 10~2022 Dec. 31.

Industrial Applicability

The present invention relates to a composite ultra-thin coating film with hypersensitivity inflammatory reaction inhibition and antibacterial activity, an implant comprising the same, and a method for preparing the same.

The invention claimed is:

1. A composite ultra-thin coating film comprising:

an inner layer in which materials selected from the group consisting of a hyaluronic acid polymer (HA), a polymer represented by the following Formula 1, and poly(allylamine hydrochloride) (PAH) are alternately laminated; and an outermost layer in contact with cells, wherein the outermost layer is laminated with a hyaluronic acid polymer (HA) or a polymer represented by the following Formula 1:

[Formula 1]

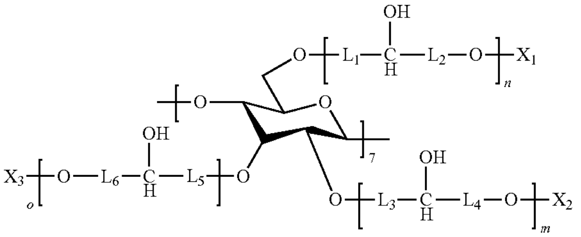

[Formula 2]

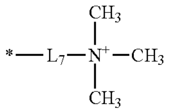

[Formula 3]

$*-L_8-COO^-H^+$ where,

*refers to a part that is combined, n, m, and o are the same as or different from each other and are each independently an integer of 1 to 100, $L_1$ to $L_8$ are the same as or different from each other, and are each independently a single bond or a substituted or unsubstituted alkylene group having 1 to 10 carbon atoms, and $X_1$ to $X_3$ are the same as or different from each other, and are each independently selected from the group consisting of cyclodextrin, a compound represented by Formula 2 above, and a compound represented by Formula 3 above.

2. The composite ultra-thin coating film of claim 1, wherein the compound represented by Formula 1 above is a cationic polymer (Cat-CyD) including the compound represented by Formula 2 above, and is alternately laminated with hyaluronic acid (HA) or poly(allylamine hydrochloride) (PAH).

3. The composite ultra-thin coating film of claim 2, wherein the compound represented by Formula 1 above is an anionic polymer (Ani-CyD) including the compound represented by Formula 3 above, and is alternately laminated with the cationic polymer (Cat-CyD).

4. The composite ultra-thin coating film of claim 3, wherein the inner layer is [PAH/HA], [PAH/Cat-CyD], [Cat-CyD/HA], or [Cat-CyD/Ani-CyD] laminated in a plurality.

5. The composite ultra-thin coating film of claim 4, wherein the inner layer is formed by laminating [PAH/HA], [PAH/Cat-CyD], [Cat-CyD/HA] or [Cat-CyD/Ani-CyD] in a plurality, and then additionally laminating [Cat-CyD].

6. The composite ultra-thin coating film of claim 1, wherein the inner layer has a pH of 3 to 5.

7. The composite ultra-thin coating film of claim 1, wherein the composite ultra-thin coating film inhibits the formation of a biofilm produced by *Staphylococcus epidermidis*.

8. The composite ultra-thin coating film of claim 1, wherein the composite ultra-thin coating film inhibits malformed cell proliferation.

9. The composite ultra-thin coating film of claim 1, wherein the composite ultra-thin coating film has a thickness of 20 nm or less.

10. A method for preparing a composite ultra-thin coating film comprising steps of:

forming an inner layer by alternately laminating materials selected from the group consisting of a hyaluronic acid polymer (HA), a polymer represented by the following Formula 1, and poly(allylamine hydrochloride) (PAH); and forming an outermost layer in contact with cells by laminating the hyaluronic acid polymer (HA) or the polymer represented by the following Formula 1:

[Formula 1]

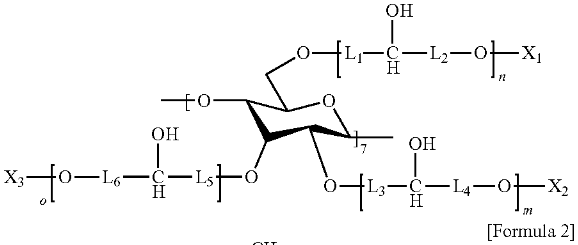

[Formula 2]

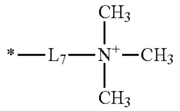

[Formula 3]

$*-L_8-COO^-H^+$ where,

*refers to a part that is combined, n, m, and o are the same as or different from each other and are each independently an integer of 1 to 100, $L_1$ to $L_8$ are the same as or different from each other, and are each independently a single bond or a substituted or unsubstituted alkylene group having 1 to 10 carbon atoms, and $X_1$ to $X_3$ are the same as or different from each other, and are each independently selected from the group consisting of cyclodextrin, a compound represented by Formula 2 above, and a compound represented by Formula 3 above.

11. The method of claim 10, wherein the inner layer is formed under conditions of pH 3 to 5.

12. An implant comprising:

a substrate; and the composite ultra-thin coating film according to claim 1 formed on a surface of the substrate.

13. The implant of claim 12, wherein the substrate is a silicone-based polymer or metal.

14. A method for manufacturing an implant on which a composite ultra-thin coating film is formed comprising steps of:

forming an inner layer by alternately laminating materials selected from the group consisting of a hyaluronic acid polymer (HA), a polymer represented by the following Formula 1, and poly(allylamine hydrochloride) (PAH) on a substrate; and forming an outermost layer in contact with cells by laminating the hyaluronic acid polymer (HA) or the polymer represented by the following Formula 1:

[Formula 1]

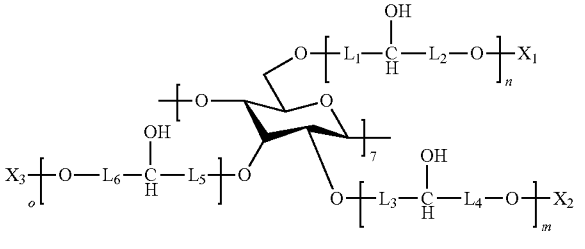

-continued

[Formula 2]

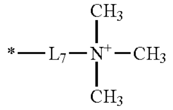

[Formula 3]

$$*-L_8-COO^-H^+$$

where,

* refers to a part that is combined, n, m, and o are the same as or different from each other and are each independently an integer of 1 to 100, $L_1$ to $L_8$ are the same as or different from each other, and are each independently a single bond or a substituted or unsubstituted alkylene group having 1 to 10 carbon atoms, and $X_1$ to $X_3$ are the same as or different from each other, and are each independently selected from the group consisting of cyclodextrin, a compound represented by Formula 2 above, and a compound represented by Formula 3 above.

15. A contact lens for ophthalmic surgery comprising:

a silicone-based polymer substrate; and the composite ultra-thin coating film according to claim 1 formed on a surface of the substrate.

* * * * *